US009345839B2

(12) United States Patent
Shetty et al.

(10) Patent No.: US 9,345,839 B2
(45) Date of Patent: May 24, 2016

(54) ACCURATE DOSE CONTROL MECHANISMS AND DRUG DELIVERY SYRINGES

(71) Applicant: Unitract Syringe Pty Ltd, Sydney (AU)

(72) Inventors: Gautam N. Shetty, Pikesville, MD (US); Lou Castagna, Middletown, PA (US)

(73) Assignee: UNITRACT SYRINGE PTY LTD, Sydney (AU)

(*) Notice: Subject to any disclaimer, the term of this patent is extended or adjusted under 35 U.S.C. 154(b) by 625 days.

(21) Appl. No.: 13/707,201

(22) Filed: Dec. 6, 2012

(65) Prior Publication Data

US 2013/0150803 A1    Jun. 13, 2013

Related U.S. Application Data

(60) Provisional application No. 61/568,509, filed on Dec. 8, 2011.

(51) Int. Cl.
*A61M 5/00*    (2006.01)
*A61M 5/315*   (2006.01)
(Continued)

(52) U.S. Cl.
CPC ............. *A61M 5/31526* (2013.01); *A61M 5/28* (2013.01); *A61M 5/31575* (2013.01); *A61M 2005/3139* (2013.01); *A61M 2005/3152* (2013.01); *Y10T 29/49826* (2015.01)

(58) Field of Classification Search
CPC ................... A61M 5/31528; A61M 5/31575; A61M 5/31533
USPC ................................................. 604/207–211
See application file for complete search history.

(56) References Cited

U.S. PATENT DOCUMENTS

| 2,943,624 | A |   | 7/1960 | Alquist |
| 3,596,659 | A | * | 8/1971 | Glasser ................. 604/187 |

(Continued)

FOREIGN PATENT DOCUMENTS

| AU | 2009217376 A1 | 10/2009 |
| DE |   10235468 A1 | 4/2003 |

(Continued)

OTHER PUBLICATIONS

European Patent Office, International Search Report in International Application No. PCT/US2012/068210, 6 pages (Apr. 24, 2013).

(Continued)

*Primary Examiner* — Emily Schmidt
*Assistant Examiner* — Deanna K Hall
(74) *Attorney, Agent, or Firm* — Leydig, Voit & Mayer, Ltd.

(57) ABSTRACT

A dose control mechanism for a syringe includes a plunger having a coarse pitch screw on its exterior surface, a housing having a corresponding coarse pitch guide along the interior surface of the housing, a screw having a fine pitch screw which interfaces with a fine pitch nut of an adapter, wherein the plunger has an internal annular space within which screw at least partially resides. An accurate dose drug delivery syringe includes such a dose control mechanism, a barrel, a plunger seal, and a barrel adapter assembly having a barrel tip and a needle. The syringe may be a fill-at-time-of-use syringe, a pre-filled syringe, or a safety syringe having integrated needle retraction or needle sheathing safety features, or a combination thereof. Methods of assembly, manufacturing, and operation are similarly disclosed.

14 Claims, 8 Drawing Sheets

(51) Int. Cl.
*A61M 5/28* (2006.01)
*A61M 5/31* (2006.01)

(56) References Cited

U.S. PATENT DOCUMENTS

| | | |
|---|---|---|
| 4,018,223 A | 4/1977 | Ethington |
| 4,444,335 A | 4/1984 | Wood et al. |
| 4,465,478 A | 8/1984 | Sabelman et al. |
| 4,687,472 A | 8/1987 | Gross |
| 4,865,591 A | 9/1989 | Sams |
| 4,936,833 A | 6/1990 | Sams |
| 5,115,816 A | 5/1992 | Lee |
| 5,135,511 A | 8/1992 | Houghton et al. |
| 5,250,030 A | 10/1993 | Corsich |
| 5,346,475 A | 9/1994 | Gregorio |
| 5,378,233 A | 1/1995 | Haber et al. |
| 5,531,691 A | 7/1996 | Shonfeld et al. |
| 5,562,623 A | 10/1996 | Shonfeld et al. |
| 5,582,595 A | 12/1996 | Haber et al. |
| 5,819,983 A | 10/1998 | White et al. |
| 5,971,227 A | 10/1999 | White et al. |
| 6,231,550 B1 | 5/2001 | Laughlin |
| 6,283,941 B1 | 9/2001 | Schoenfeld et al. |
| 6,533,756 B2 | 3/2003 | Schoenfeld et al. |
| 6,719,735 B1 | 4/2004 | Gammon |
| 6,957,752 B2 | 10/2005 | Py et al. |
| 7,290,573 B2 | 11/2007 | Py et al. |
| 7,500,959 B2 | 3/2009 | Munk |
| 7,611,495 B1 | 11/2009 | Gianturco |
| 7,798,185 B2 | 9/2010 | Py et al. |
| 7,857,791 B2 | 12/2010 | Jacobs et al. |
| 7,867,202 B2 * | 1/2011 | Moser et al. ............ 604/209 |
| 7,959,609 B2 | 6/2011 | Gaydos et al. |
| 7,967,772 B2 | 6/2011 | McKenzie et al. |
| 8,057,427 B2 | 11/2011 | Griffiths et al. |
| 2003/0004467 A1 | 1/2003 | Musick et al. |
| 2005/0215958 A1 | 9/2005 | Hawthorne |
| 2009/0275914 A1 * | 11/2009 | Harms et al. ............ 604/506 |
| 2010/0305512 A1 | 12/2010 | Guillermo et al. |
| 2010/0331808 A1 | 12/2010 | Py et al. |

FOREIGN PATENT DOCUMENTS

| | | |
|---|---|---|
| EP | 0295075 A1 | 12/1988 |
| EP | 0862731 A1 | 9/1998 |
| EP | 0937471 A2 | 8/1999 |
| EP | 2162230 B1 | 11/2010 |
| FR | 2583291 A1 | 12/1986 |
| GB | 2140302 A | 11/1984 |
| JP | 2000-296178 A | 10/2000 |
| WO | WO 97/19327 A1 | 5/1997 |
| WO | WO 99/38554 A1 | 8/1999 |
| WO | WO 2006/108243 A2 | 10/2006 |
| WO | WO 2006/119570 A1 | 11/2006 |
| WO | WO 2006/125329 A1 | 11/2006 |
| WO | WO 2009/003234 A1 | 1/2009 |
| WO | WO 2010/063687 A1 | 6/2010 |
| WO | WO 2011/075760 A1 | 6/2011 |
| WO | WO 2011/137488 A1 | 11/2011 |

OTHER PUBLICATIONS

European Patent Office, Written Opinion of the International Searching Authorty in International Application No. PCT/US2012/068210, 8 pages (Apr. 24, 2013).

* cited by examiner

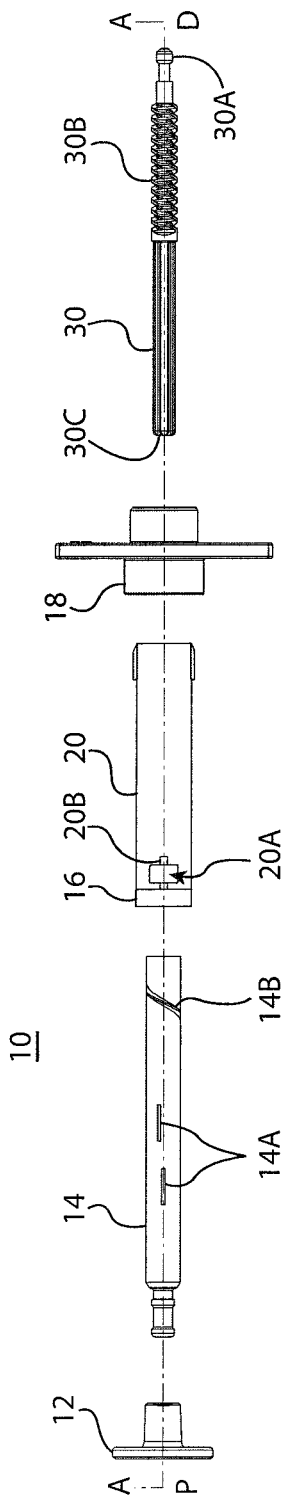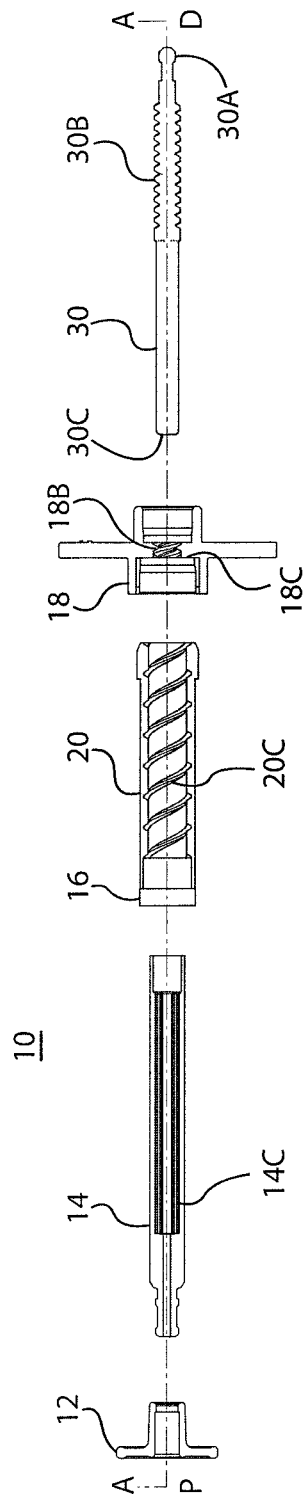

ACCURATE DOSE CONTROL MECHANISMS AND DRUG DELIVERY SYRINGES

CROSS-REFERENCE TO RELATED APPLICATIONS

This application claims priority to U.S. Provisional Application No. 61/568,509, filed on Dec. 8, 2011, which is included by reference herein in its entirety for all purposes.

FIELD

THIS INVENTION relates to accurate dose drug delivery syringes. More particularly, this invention relates to accurate dose control mechanisms, drug delivery syringes which incorporate such control mechanisms, the methods of operating such devices, and the methods of assembling such devices.

BACKGROUND

Various studies have shown that the accuracy of dose delivery is affected by a number of factors, including: injection methodologies employed by medical practitioners, an inability to accurately read and control plunger travel during dosing, and the loss of dosage associated with the prime step used to evacuate air from the syringe prior to the dosing step. These effects are particularly magnified by the use of drug delivery syringes that have a high dose volume to axial translation ratio (i.e., a significant quantity of drug is dispensed for even incrementally small distances of plunger depression, as may be the case for large diameter syringes); this problem is more acute when delivering microliter size doses. While these causes for error are common, the need for accurate dose syringes remains. Such syringes are of particular importance in sensitive operations, such as in intravitreal injections, and are very desirable for low dose treatments where inaccurate dosing can lead to substantial error and potential patient harm.

Studies have shown that the amount of treatment delivered may vary significantly depending on whether the medical practitioner chooses to deliver 5 µL (5 microliters) of the treatment by depressing the syringe plunger from 10 µL to 5 µL or by depressing the syringe from 5 µL to 0 µL. Additionally, due to the uncertainty of plunger travel limits some practitioners may depress the syringe past the natural travel limit and deliver excess treatment to the patient because of mechanical compliance between the stopper and the syringe barrel. For example, given a particular syringe barrel diameter, a practitioner may depress the plunger past the natural stop for 0 µL and erroneously deliver up to 20% more dosage than necessary. This error is magnified because of the small dose volume requirements for particular treatments. Because the dosage amount and associated plunger travel distance are small, it is very difficult for a practitioner to gauge the fill amount of the dosing chamber and to control the injection amount as the treatment is applied to the patient. This inaccuracy in dosing can lead to substantial safety risks including, among other side effects, increased pressure in the target region and altered (reduced) drug efficacy.

A primary cause of the dosing inaccuracy is the inability to reliably set the limits of plunger travel, and the inherent variability in the degree to which the plunger seal (or stopper) is depressed at end of delivery during dosing. Also contributing to inaccuracy is the potential variability, during syringe manufacturing, in the placement of reference markings on the syringe barrel. Endemic to these causes of inaccuracy is the high sensitivity of volume dispensed to the axial travel of the plunger, as described above. Mechanical travel limits, however, are difficult to employ in such applications because of the challenges associated with reading and controlling the plunger travel by the user over the small distance of dosing. Simply put, because the dosage amounts are so small, it is difficult for a practitioner to identify the dosage measurements on the syringe barrel and accurately control the plunger depression and dosage amount during injection.

In addition to improving dosing accuracy, it is useful to incorporate the functionality of a priming step into a syringe design to reduce or eliminate air bubbles within the dosing chamber. This step is very useful to minimize safety risks, improve operational hygiene, and reduce pressure in the target site. Minimizing the likelihood of air bubbles during filling helps streamline the drug delivery process for the clinician. Employing pre-filled syringes may assist in the minimization of air bubbles. However, even pre-filled syringes are not fully devoid of air captured during the filling process.

Accordingly, there is a substantial need for syringes which allow the user to readily identify and control the dosage amount, minimize the presence of air bubbles within the dosage chamber prior to drug delivery, and ensure accurate delivery of the required drug dose. It is preferred that such a syringe would enable pre-filling to take advantage of benefits associated with the use of such products.

SUMMARY

The present invention provides dose control mechanisms, which allow for the accurate dosing and delivery of drug treatments, and drug delivery syringes which incorporate such control mechanisms. Such novel devices permit the identification and control of the dosage amount, permit the syringe to be "primed" (i.e., evacuated of air bubbles) prior to drug delivery, and ensure the accurate delivery of microliter volume dosages, all within a device size that is similar to commonly used conventional syringes available in the marketplace. Such novel devices are safe and easy to use, and are aesthetically and ergonomically appealing for clinical practitioners without significantly altering technique currently employed by clinicians to administer injectable medications. The novel devices of the present invention provide these desirable features without any of the problems associated with known prior art devices.

In a first embodiment, the present invention provides a dose control mechanism for a syringe. The control mechanism includes a plunger having a coarse pitch screw on its exterior surface, a housing having a corresponding coarse pitch guide along the interior surface of the housing, a screw having a fine pitch screw which interfaces with a fine pitch nut of an adapter, wherein the plunger has an internal annular space within which screw at least partially resides. The plunger having the coarse pitch is rotatable upon the corresponding coarse pitch guide, and wherein at least a portion of the plunger is rotationally keyed to interface with a corresponding rotationally keyed portion of screw. A pitch ratio between the coarse pitch screw and the fine pitch screw is from approximately 1:1 to approximately 20:1, more specifically from approximately 2:1 to approximately 10:1, and more preferably from approximately 4:1 to approximately 8:1. In a preferred embodiment, the pitch ratio of the coarse pitch screw 14B and the fine pitch screw 30B is approximately 4:1. The screw may further include a screw connection aspect and, optionally, a ring which function to connect the screw to the plunger seal directly or to a plunger rod. In at least one embodiment, the housing has a housing cover at its proximal end and a window to permit the user to view the location of the plunger within housing. The plunger may have one or more dose markings on the external surface of the plunger and the housing may have one or more guide markings with which to align plunger dose markings. Upon use by the user, plunger axially translates a first distance D1 causing screw to axially translate a second distance D2, wherein D1 is always greater than D2 by a factor determined by the pitch ratio.

In a second embodiment, the present invention provides an accurate dose drug delivery syringe having a dose control mechanism, a barrel, a plunger seal, and a barrel adapter assembly having a barrel tip and a needle. The syringe may further include a plunger rod connected at one end to screw and at another end to plunger seal. The syringe may be a fill-at-time-of-use syringe, a pre-filled syringe, or a safety syringe, or a combination thereof. The housing of the syringe may have a housing cover at its proximal end to protect the interior of the housing from the environment and a window to permit the user to view the location of the plunger within housing. The plunger may have one or more dose markings on the external surface of the plunger, and the housing may have one or more guide markings at the window with which to align plunger dose markings. Upon use by the user, plunger axially translates a first distance D3 causing screw to axially translate a second distance D4.

In a further embodiment, a method of manufacturing a syringe having a control mechanism includes the steps of: (i) mounting a barrel adapter assembly to a distal end of a syringe barrel; (ii) mounting a plunger seal through a proximal end of the syringe barrel; and (iii) mounting a control mechanism to the proximal end of the syringe barrel, wherein the control mechanism may rest in contact with the plunger seal. The method may further include, before the step of (ii) mounting a plunger seal through a proximal end of the syringe barrel, the step of: filling the barrel at least partially with a fluid substance. In at least one embodiment, the adapter is a two component adapter having a proximal adapter portion and a distal adapter portion. The proximal adapter portion has one or more connection prongs and the distal adapter portion has corresponding connection ports which, when forced together, connection prongs and corresponding connection ports merge, mate, or otherwise connect to unite the two portions of the adapter. Steps (i) and (ii), and the optional step of filling the barrel at least partially with a fluid substance, may be performed in a sterile environment to maintain the container integrity and sterility of the syringe.

The present invention further provides methods of assembling dose control mechanisms, methods of manufacturing syringes having dose control mechanisms, and methods of operation of such mechanisms and syringes. Such novel devices and methods permit the identification and control of the dosage amount, permit the syringe to be "primed" (i.e., evacuated of air bubbles) prior to drug delivery, and ensure the accurate delivery of microliter volume dosages, all within a device size that is similar to commonly used conventional syringes available in the marketplace. Throughout this specification, unless otherwise indicated, "comprise," "comprises," and "comprising," or related terms such as "includes" or "consists of" are used inclusively rather than exclusively, so that a stated integer or group of integers may include one or more other non-stated integers or groups of integers. As will be described further below, the embodiments of the present invention may include one or more additional components which may be considered standard components in the industry of medical devices. The components, and the embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein:

FIG. 3A shows an exploded view, exploded along an axis "A," of the dose control mechanism shown in FIG. 1A;

FIG. 3B shows a cross-sectional exploded view, exploded along an axis "A," of the dose control mechanism shown in FIG. 1A;

DETAILED DESCRIPTION

Figure 1A:
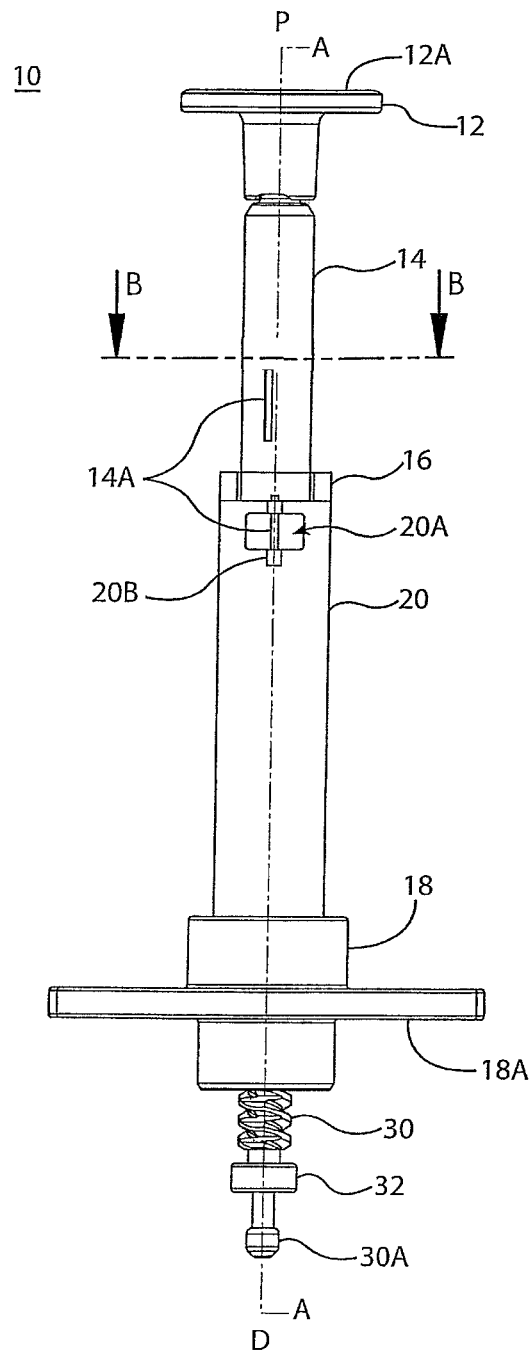
FIG. 1A shows an isometric view of a dose control mechanism, according to at least one embodiment of the present invention.

As used herein to describe the dose control mechanisms, drug delivery syringes, or any of the relative positions of the components of the present invention, the terms "axial" or "axially" refer generally to a longitudinal axis "A" around which the control mechanisms and syringes are preferably positioned, although not necessarily symmetrically therearound. The term "radial" refers generally to a direction normal to axis "A". The terms "proximal," "rear," "rearward," "back," or "backward" refer generally to an axial direction in the direction "P". The terms "distal," "front," "frontward,"

"depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC), cyclic olefin polymers (COP), and the like. The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of syringes. According to various aspects and embodiments described herein, reference is made to a "biasing member", such as in the context of one or more biasing members for retraction of a needle or needle assembly. It will be appreciated that the biasing member may be any member that is capable of storing and releasing energy. Non-limiting examples include a spring, such as for example a coiled spring, a compression or extension spring, a torsional spring, and a leaf spring, a resiliently compressible or elastic band, or any other member with similar functions. In at least one embodiment of the present invention, the biasing member is a spring, preferably a compression spring.

The novel devices of the present invention provide dose control mechanism, which allow for the accurate dosing and delivery of drug treatments, and drug delivery syringes which incorporate such control mechanisms. Such devices are safe and easy to use, and are aesthetically and ergonomically appealing for clinical practitioners. The devices described herein incorporate features which make activation, operation, and lock-out of the device simple for even untrained users. The novel devices of the present invention provide these desirable features without any of the problems associated with known prior art devices. Certain non-limiting embodiments of the novel dose control mechanisms, drug delivery syringes, and their respective components are described further herein with reference to the accompanying figures.

Various studies have shown that the accuracy of dose delivery using conventional syringes is affected by a number of factors, including an inability to accurately read and control plunger travel during dosing. The use of conventional drug delivery syringes that have a high dose volume to axial translation ratio (i.e., a significant quantity of drug is dispensed for even incrementally small distances of plunger depression, as may be the case for large diameter syringes) significantly magnifies this inaccuracy. With the growth of high-cost, low-volume drug treatments entering the marketplace, it is increasingly important to accurately dose and deliver such low-volume treatments to the patient. The embodiments of the present invention overcome the challenges faced with the use of conventional syringes for the dosing and delivery of low-volume treatments by utilizing novel dose control mechanisms. As will be described further herein, the novel dose control mechanisms permit the user to accurately read and dose the desired volume of drug treatment for delivery to the patient. These devices permit the user to have a normal range of thumb travel, as they may otherwise expect with a conventional syringe, but transform that range of thumb travel to a very finite (e.g., smaller or incremental) range of plunger seal travel. This relationship allows the user to utilize the syringe without additional training, but with the significant benefit of incremental, low-volume dose control.

FIG. 1A shows an embodiment of a novel dose control mechanism for a syringe, according to at least one embodiment of the present invention. The control mechanism 10 includes a plunger 14, a housing 20, an adapter 18, and a screw 30. The plunger 14 may include a button 12 as a unified or separate component. For example, button 12 may be a preformed aspect at the proximal end of the plunger 14. Alternatively, button 12 may be a separate component attached to the proximal end of plunger 14 by a snap-fit. In a preferred embodiment, the button 12 may be attached to plunger 14 but allowed to axially rotate freely from plunger 14, but rotationally fixed relative to the user's/clinician's finger. Regardless of the specific configuration and relationship of button 12 and plunger 14, button 12 is intended to have a user interface surface 12A for contact and control by a user (e.g., such as with the thumb or finger tip of the user).

Housing 20 has a substantially cylindrical axial pass-through within which a substantially cylindrical plunger 14 may at least partially reside. The distal end of the housing 20 is connected to, and/or resides partially within, a proximal portion of adapter 18. The proximal and distal portions of adapter 18 may be separated by an adapter flange 18A which may additionally serve as a finger flange for use by the user. The internal aspects of these components will be described in further detail herein with reference to FIGS. 1B, 2A, 2B, and 3B. Screw 32 may reside at least partially within housing 20 and plunger 14, and extends distally beyond flange 18. Screw 30 may have a screw connection 30A aspect and, optionally, a ring 32, to facilitate integration of the control mechanism with a drug delivery syringe and to center the plunger rod.

Housing 20 may optionally include housing cover 16 at its proximal end, for example, to close the interior of the housing 20 off from the environment and/or to axially align plunger 14 within housing 20, and to prevent removal of the plunger rod by functioning as a mechanical stop. Housing 20 may further include a window 20A, which may be an opening (e.g., an aperture) in the housing or a transmissive or translucent component. Regardless of the particular configuration of window 20A, its primary purpose is to permit the user to view the location of the plunger 14 within housing 20. Plunger 14 may include one or more dose markings 14A on the external surface of the plunger 14. Housing 20 may have one or more reference or guide markings 20B, such as at the window 20A, with which to align plunger dose markings 14A. The plunger dose markings 14A may correspond to the relevant dose amounts desired by the user. By employing the respective plunger and housing markings, the user can control the volumetric dose quantities desired for delivery to the patient, as will be explained further herein. In another embodiment, the window 20A may be covered by a lens, such as a clear lens, that provides visual magnification.

Figures 2A, 2B:
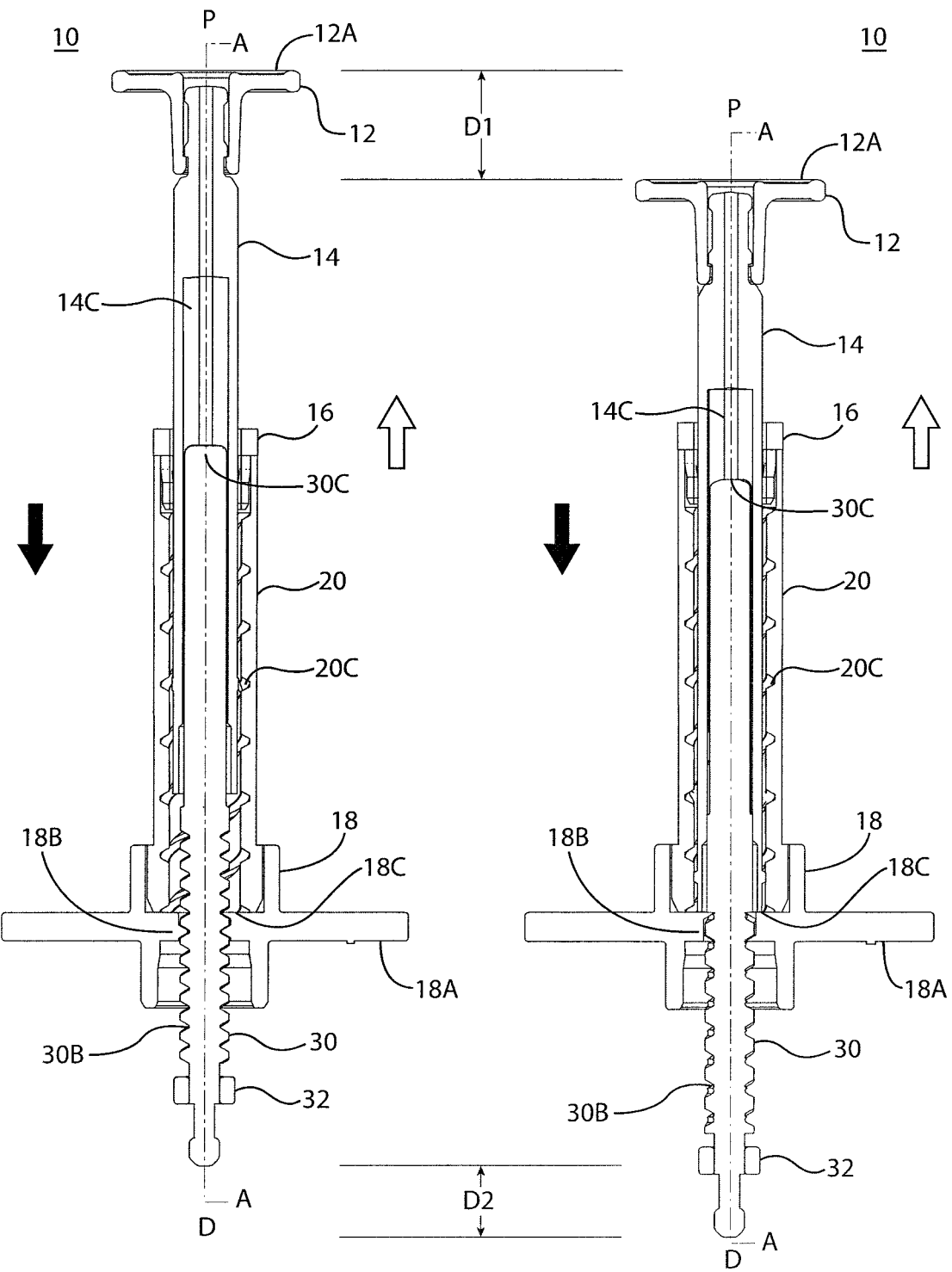
FIG. 2A shows a cross-sectional view of the dose control mechanism shown in FIG. 1A as the components may appear in a ready-to-inject stage of operation.
FIG. 2B shows a cross-sectional view of the dose control mechanism shown in FIG. 1A as the components may appear in an end-of-dose stage of operation.

FIGS. 2A and 2B show cross-sectional views of the dose control mechanism, according to at least one embodiment of the present invention, in a ready-to-inject stage and in an end-of-dose stage, respectively. The cross-sectional views show certain other aspects of the components which are internal to the mechanism. As shown, plunger 14 has an internal annular space 14C within which screw 30 at least partially resides. Plunger 14 has a coarse pitch male thread 14B (visible in FIG. 3A) on its exterior surface which interfaces with the coarse pitch guide 20C along the interior surface of the housing 20 such that, in at least one embodiment, the pitch on guide 20C is the same as pitch on plunger thread 14B. Similarly, screw 30 has a fine pitch thread 30B which interfaces with a fine pitch nut 18B of adapter 18 such that, in at least one embodiment, the pitch on screw thread 30B is the same as pitch on nut 18B. Also visible in FIGS. 2A and 2B are the proximal end 30C of screw 30 and ledge 18C of adapter 18. The plunger 14 having the coarse pitch 14B is rotatable upon the corresponding (e.g., "female") coarse pitch guide 20C, which is rotationally keyed to the screw 30 having the fine pitch thread 30B. The terms "male" and "female" are intended to describe corresponding and interfacing threads or surfaces, and can be used interchangeably to describe corresponding aspects as would be readily appreciated in the art. The screw 30 having the fine pitch screw 30B engages the female fine pitch nut 18B of the adapter 18. Hence, rotation of plunger 14 results in axial translation of screw 30 and the resolution of axial travel is dictated by pitch 30B.

Figure 1B:
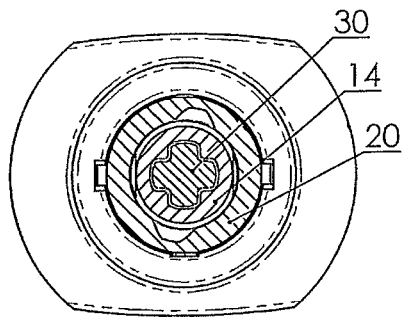
FIG. 1B shows a cross-sectional view in a plane "B" which is perpendicular to axis "A" of the dose control mechanism of FIG. 1A.

Because the plunger 14 and screw 30 are rotationally keyed, each having a respective screw pitch, rotational translation of the plunger 14 rotates and axially translates the screw 30. The term "keyed" is used herein to mean any number of internal aspects which removably or slidably (in the axial sense) connect two or more components. For example, the plunger 14 may be a hollow cylinder having a coarse pitch screw on at least some portion of the outer surface and a spline design along at least a portion of the inner surface. The spline design is configured to mate with, and transform or relay rotation to, a complimentary spline contained at a proximal end of the screw 30. This spline design element ensures that the plunger 14 and screw 30 are rotationally keyed. The spline or rotationally keyed aspect is visible at the proximal end 30C of screw 30 in FIG. 3A, and with its corresponding spline or rotationally keyed aspect in the annular space 14C of plunger 14 in FIG. 3B. Any number of corresponding shapes may be utilized to impart a rotationally "keyed" relationship between these components such that the first component may removably or slidably engage the second component in a manner which enables the rotational keyed relationship and permits axial slip. Such components may alternatively be keyed to have the shape of, for example, a cross or plus, a horizontal line or minus, a star, or a semi-circle shape, with the corresponding component having the inverse of the shape on an interior annular space. FIG. 1B shows a cross-sectional view in a plane "B" which is perpendicular to axis "A" of the dose control mechanism of FIG. 1A. As shown in FIG. 1B, in at least one embodiment, screw 30 has a cross or plus shape in its perpendicular cross-section which is keyed to plunger 14. This arrangement or configuration allows the two components to be rotationally keyed while allowing them to axially slip past each other. Both screw 30 and plunger 14 reside, at least partially and/or at some point of operation, within housing 20.

Fine pitch nut 18B (or simply "nut"), having the same fine pitch of the screw 30, may be used to brace the screw 30 and facilitate the transfer of the rotational movement of the plunger 14 into axial translation of the screw 30. The pitch ratio of the coarse pitch to the fine pitch dictates the degree or resolution of axial travel of the screw 30, i.e., the distance that the screw 30 axially translates for each rotation of the plunger 14. As a result, the medical practitioner is provided with an ease of operation that enables them to accurately read and set the dosage amount. The pitch ratio can be set to enable "fine tuning" of the dosage amount, which is of particular importance for low-volume dosage quantities where variance may be significantly affected by plunger travel.

During operation of the dose control mechanism, the user may axially rotate plunger 14 or depress the button 12 to control the desired dosage volume for injection into the patient. Axial rotation of the plunger 14 causes coarse pitch screw 14B (visible in FIG. 3B) to travel within the corresponding coarse pitch guide 20C of housing 20, as shown in FIGS. 3A and 3B. This action causes the plunger 14 to axially translate in the distal direction thereby reducing the dosage volume within the drug chamber, as is explained in more detail herein. Because of the rotationally keyed interaction between plunger 14 and screw 30 within the annular space 14C, rotation of the plunger 14 causes screw 30 to axially rotate and translate. However, because of the pitch ratio between the plunger 14 and screw 30, each unit measure of translation in the distal direction of the plunger 14 results in fractional (e.g., smaller, more resolved) translation of the screw 30 in the distal direction. This has a number of benefits for accurate control during delivery of low-volume doses. Primarily, the pitch ratio relationship permits the user to accurately control the desired dose and delivery of a drug treatment. Additionally, this pitch ratio relationship allows the user to operate a syringe in a conventional manner, such as by depressing the plunger 14 a noticeable distance, while only resulting in fractional or small translation of the screw.

The novel dose control mechanisms of the present invention also utilize features which provide integrated and adjustable range-of-travel limits to ensure accurate delivery of low-volume drug treatments. This may be enabled, for example, by incorporating features that prevent variable depression of the plunger seal (or stopper) (e.g., preventing the plunger from "bottoming out" during drug delivery) within a syringe. Specifically, the dose control mechanisms of the present invention utilize adjustable set mechanical end-points for the range of plunger axial travel during drug delivery. Such limits may be predefined, i.e., integrated and fixed into the syringe configuration in advance of use by the medical practitioner, or adjustable, i.e., variably controlled by a compounding pharmacist, a medical practitioner, or by a self-administering patient using an integrated dosage setting mechanism. Such mechanical set-points permit a range of axial plunger travel that are, for example, related to the priming and dosing quantities, but also prevent the user from variably depressing the plunger and plunger seal as part of the dosing stroke or from bottoming out these components within the dosing chamber of a syringe. This novel control mechanism greatly increases the accuracy of the dose delivered to the patient. Additionally, embodiments of the present invention allow the user to prime the syringe to evacuate the dosing chamber of any residual air prior to delivering the dose to the patient. The prime step may be a fixed amount or a variable amount, depending on the configuration of the low dose syringe and variation in amount of drug or liquid contained/filled in the dosing chamber. The configuration of the novel syringe allows the user to complete the prime step while maintaining, or enabling, the ability of the syringe to deliver an accurate and precise dose to the patient.

As stated above, the mechanical set-point limits effectively function to prevent the user from variably depressing the plunger and plunger seal or from bottoming out these components within the dosing chamber of a syringe. This functionality increases the accuracy of the dose delivered to the patient because it reduces the variability of the delivered dose from the amount prescribed and intended to be delivered to the patient. The mechanical end-points may be readily identified and easily set by employing the pitch ratio between the plunger 14 having a coarse pitch screw 14B and the screw 30 having a fine pitch screw 30B. For example, in one such embodiment a pitch ratio between the coarse pitch and a fine pitch may be 4:1, such that rotationally "screwing" or turning plunger 14 axially translates the plunger component four times as far as the axial translation of the screw component. Accordingly, the practitioner is provided with a significant ease of operation since they may more accurately set the required dosage amount. Such a pitch ratio may be, for example, anywhere from the range of 1:1 to 20:1, as may be necessary to obtain the required accuracy of the low-volume dosage amount. The "dialing-in" or "setting" may be facilitated by the dose markings on the plunger and guide markings on the housing described above.

As the user depresses the button 12, which rotates the plunger 14 to set the desired low-volume dosage for injection, they can perform what is known in the art as a "priming step." This priming step evacuates the dosing chamber of any residual air bubble captured in the dosing chamber during pre-filling, if any, and primes the attached needle (or catheter or an extension set) before delivery. After priming and setting of the dose by depression of the button 12 has been completed, the button 12 may be depressed further to bottom out and, hence, inject the desired dose amount to the patient. Upon drug dose delivery, the plunger 14 is caused to "bottom out" on ledge 18C of adapter 18 (as shown in FIG. 2B). Because of the pitch ratio between the plunger 14 and the screw 30, as plunger 14 is depressed or axially translated in the distal direction (i.e., in the direction of solid arrow in FIGS. 2A and 2B), screw 30 is caused to axially translate in the distal direction only a fraction of the distance translated by the plunger 14. This difference in axial translation distance between plunger 14 and screw 30 is visible by comparing distances D1 and D2 in FIGS. 2A and 2B. D1 is the distance that plunger 14 axially translates while D2 is the incremental distance that screw 30 axially translates. The difference in dimensions D1 and D2 is also clear by the reduction in the annular space 14C of plunger 14 (compare FIGS. 2A and 2B), when identifying the relative position of the proximal end 30C of the screw 30. Accordingly, the variable annular space 14C of plunger 14 is related to the mechanical set-point desired by the practitioner and provides space for translation of the screw 30 during the dosage stroke.

Notably, the novel embodiments contemplated by the present invention effectively prevent the plunger seal from "bottoming-out" within the dosing chamber. This pre-empts one aspect of user variability in either excess dosing by over-depression of the plunger or under dosing by under-depression of the plunger, ensuring that the quantity dosed to the patient is accurate and minimizes user error. This is of particular importance in low dosage treatments, where user-related errors can cause significant and undesirable variation and inaccuracy in the delivery of medication to the patient. The embodiments according to the present invention prevent such occurrences and work to effectively eliminate the dosing errors associated with prior syringe configurations and delivery methodologies. Furthermore, depression of the plunger in this embodiment does not back-drive the screw.

The novel dose control mechanisms of the present invention can be integrated into a number of drug delivery syringe configurations to provide accurate dose delivery capability to the user. For example, the control mechanisms may be utilized with fill-at-time-of-use syringes, pre-filled syringes, or safety syringes having integrated needle retraction or needle sheathing safety features, or a combination thereof. Examples of such syringes which incorporate the novel dose control mechanisms are provided below. By employing the respective plunger 14 and, optionally, the dose markings 14A and guide markings 20B, the user can control the volumetric dose quantities within the syringe that is desired for delivery to the patient. The plunger dose markings 14A may correspond to the relevant dose amounts desired by the user. The user may initially utilize the plunger, such as by axially depressing the button or rotating the plunger, to identify and select the desired dose amount by aligning the desired dose marking 14A with the guide marking 20B. Axial rotation of the plunger 14 causes the plunger 14 to axially translate in the distal direction, which motion is transferred by the above described mechanism to the screw 30. Axial translation of the screw 30 in the distal direction causes drug fluid contained within the drug chamber of the syringe to be dispensed through the needle of the barrel adapter assembly. Once the desired dose has been identified and selected by the user, the remaining about of drug fluid within the drug chamber is substantially the exact amount desired to be injected. Syringe may then be injected into the patient for drug delivery. After injection of the needle into the patient, the user may further depress the plunger 14 (and/or the button 12) axially in the distal direction to deliver the drug dose. Because of the novel aspects of the present invention, including the pitch ratio and mechanical stop mechanisms described above, the accuracy of the dose is finely controlled and variability is reduced. In the embodiments of the present invention intended for fill-at-time-of-use syringes, the plunger 14 and screw 30 may initially function in reverse (e.g., axially translate in the proximal direction) to draw-in drug fluid from a vial or container to fill the drug chamber of the syringe. In the embodiments of the present invention intended for retractable or safety syringes, the plunger 14 and screw 30 may function, substantially after the drug dose has been delivered, to initiate or engage a needle retraction or safety mechanism. These embodiments of the present invention are discussed in further detail below with reference to the accompanying figures.

Figure 4A:
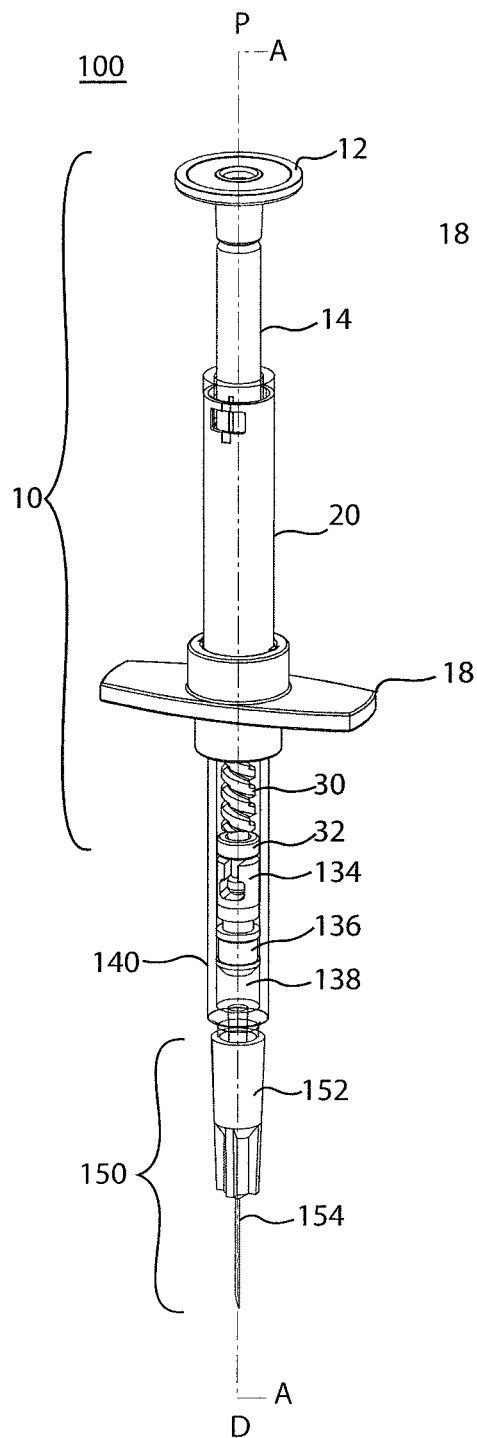
FIG. 4A shows an isometric view of a drug delivery syringe which incorporates a dose control mechanism, according to a second embodiment of the present invention.

FIG. 4A shows an embodiment of the dose control mechanism 10 as a component of an exemplary fill-at-time-of-use drug delivery syringe 100, i.e., syringes which can be drawn back and filled with a drug treatment by the user. As shown, the control mechanism 10 includes a plunger 14, a housing 20, an adapter 18, and a screw 30. The plunger 14 may include a button 12 as a unified or separate component, as described above. Housing 20 may optionally include housing cover 16 at its proximal end, for example, to close the interior of the housing 20 off from the environment and/or to axially align plunger 14 within housing 20. Housing 20 may further include a window 20A, which may be an opening (e.g., an aperture) in the housing or a transmissive, translucent, and/or optically magnifying component. Plunger 14 may include one or more dose markings 14A on the external surface of the plunger 14. Housing 20 may have one or more reference or guide markings 20B, such as at the window 20A, with which to align plunger dose markings 14A. The control mechanism 10 may be attached, mounted, affixed, or otherwise connected at the proximal end of barrel 140 such that at least a portion of the screw 30 resides inside barrel 140.

Figure 4B:
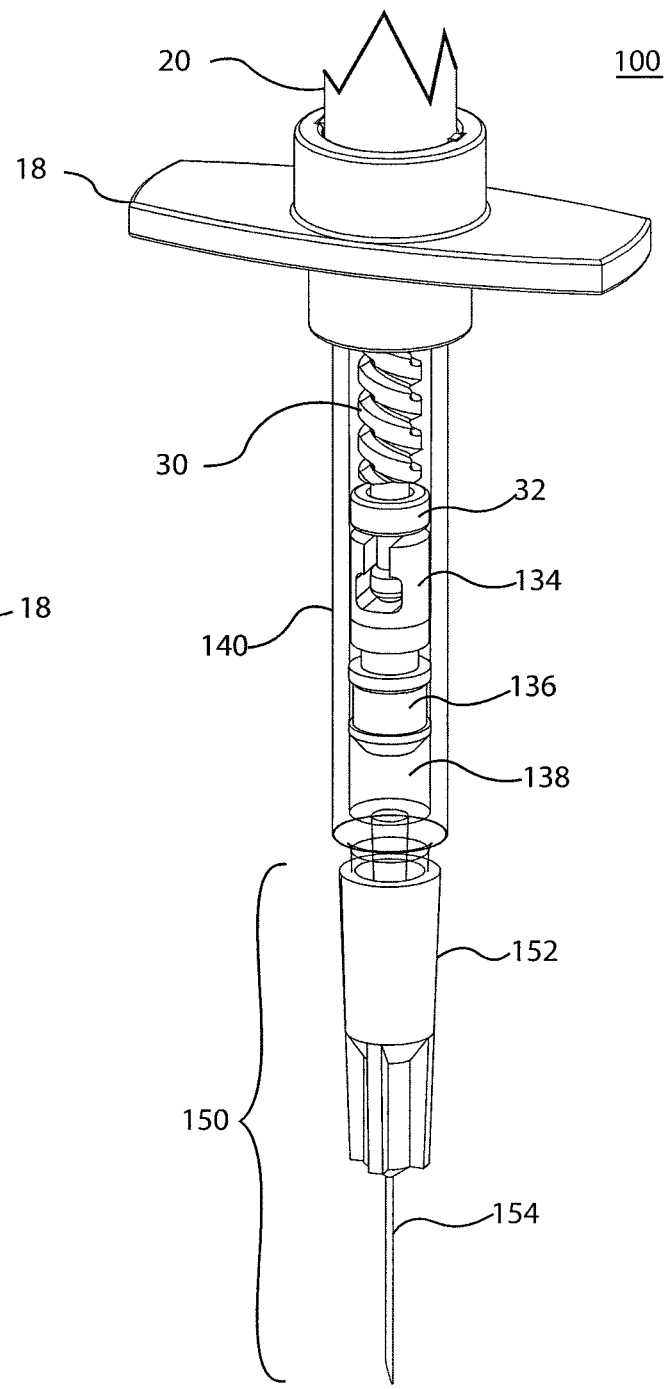
FIG. 4B shows an enlarged isometric view of the distal portion of the drug delivery syringe shown in FIG. 4A.

FIG. 4B shows an enlarged isometric view of the distal portion of the drug delivery syringe shown in FIG. 4A. Screw 30 may be connected to plunger seal 136 either directly or indirectly to drive the axial translation of the plunger seal 136. In the latter configuration, a plunger rod 134 may be utilized between screw 30 and plunger seal 136 to connect those components. The plunger rod 134 may be connected to the screw 30 at, for example, the screw connection 30A aspect. Optionally, a ring 32 near the distal end of the screw 30 may be utilized to facilitate the connection of the screw 30, the plunger rod 134 and the plunger seal 136. The screw connection 30A aspect and the ring are visible in FIGS. 2A, 2B, and 3B. In at least one embodiment, the screw connection 30A aspect is connected to the plunger rod 134 through a radial opening in the plunger rod. Additionally or alternatively, this connection may be a snap-fit connection, an interference-fit connection, or a number of other connection methods known in the industry. In at least one other embodiment, the screw connection aspect is connected to the plunger rod through a proximal opening in the plunger rod such that the screw connection aspect sits within a proximal pocket in the plunger rod. Preferably, the connection between the screw 30 and the plunger seal 136, or screw 30 and plunger rod 134 when a plunger rod is employed, is such that the screw is permitted to axially rotate while the plunger rod and/or the plunger seal remain rotationally fixed. Accordingly, as the plunger 14 and screw 30 of the control mechanism 10 are axially rotated and translated, the motion is relayed to the plunger seal 136 which is also axially translated.

When utilized within a fill-at-time-of-use syringe, the plunger 14 and screw 30 may initially function in reverse (e.g., axially translate in the proximal direction) to draw-in drug fluid from a vial or container to fill the drug chamber 138 of the syringe 100. As described above, the control mechanism 10 may then be utilized by the user to identify and select drug dose for delivery. The user may then inject the needle into the patient for drug delivery. Subsequently, the button 16 and/or plunger 14 may be depressed by the user to cause the plunger 14 and screw 30 to axially translate. Because of the function of the control mechanism and the pitch ratio, any measure of distal translation of the plunger 14 causes only an incremental measure of distal translation of the screw 30, permitting accurate dose delivery control by the user. Axial translation of the screw 30 causes axial translation of the plunger seal 136. This axial motion in the distal direction of the plunger seal 136 forces drug fluid out of drug chamber 138 of barrel 140, through the needle 154 of the barrel adapter assembly 150, for injection and delivery to the patient.

Figure 5A:
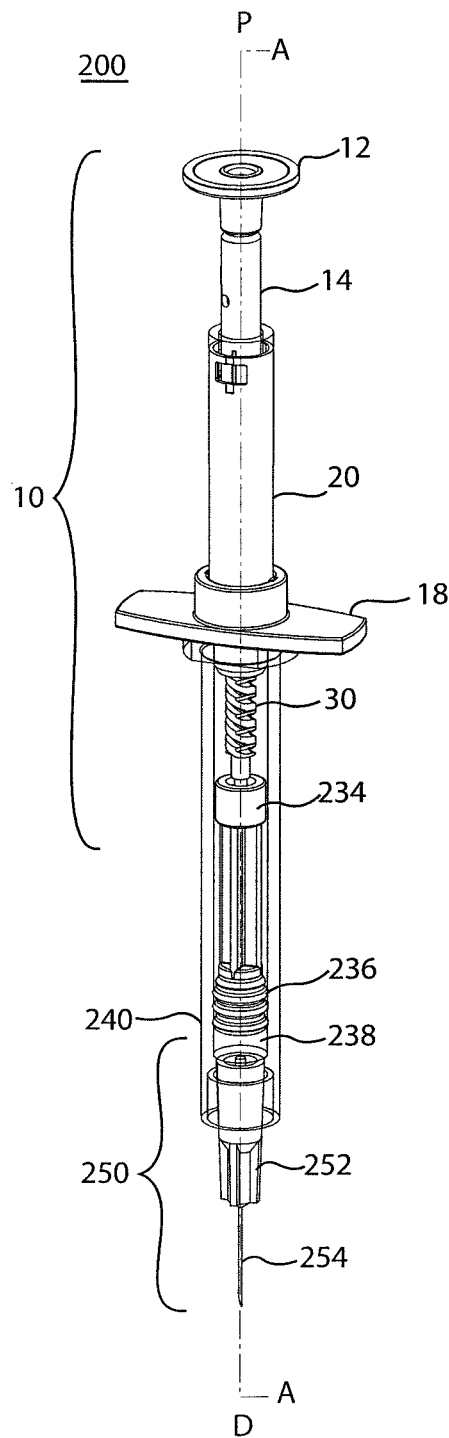
FIG. 5A shows an isometric view of another drug delivery syringe which incorporates a dose control mechanism, according to another embodiment of the present invention.

Similarly, the novel control mechanisms of the present invention may be utilized with pre-filled syringes, i.e., syringes which are filled with a drug treatment by the manufacturer and ready for injection by the user. FIG. 5A shows an embodiment of the dose control mechanism 10 as a component of an exemplary pre-filled drug delivery syringe 200. As shown, the control mechanism 10 includes a plunger 14, a housing 20, an adapter 18, and a screw 30. The plunger 14 may include a button 12 as a unified or separate component, as described above. Housing 20 may optionally include housing cover 16 at its proximal end, for example, to close the interior of the housing 20 off from the environment, to axially align plunger 14 within housing 20, and/or to prevent the plunger 14 being accidently removed by the user/clinician. Housing 20 may further include a window 20A, which may be an opening (e.g., an aperture) in the housing or a transmissive or translucent component. Plunger 14 may include one or more dose markings 14A on the external surface of the plunger 14. Housing 20 may have one or more reference or guide markings 20B, such as at the window 20A, with which to align or view plunger dose markings 14A. The control mechanism 10 may be attached, mounted, affixed, or otherwise connected at the proximal end of barrel 140 such that at least a portion of the screw 30 resides inside barrel 140.

Figure 5B:
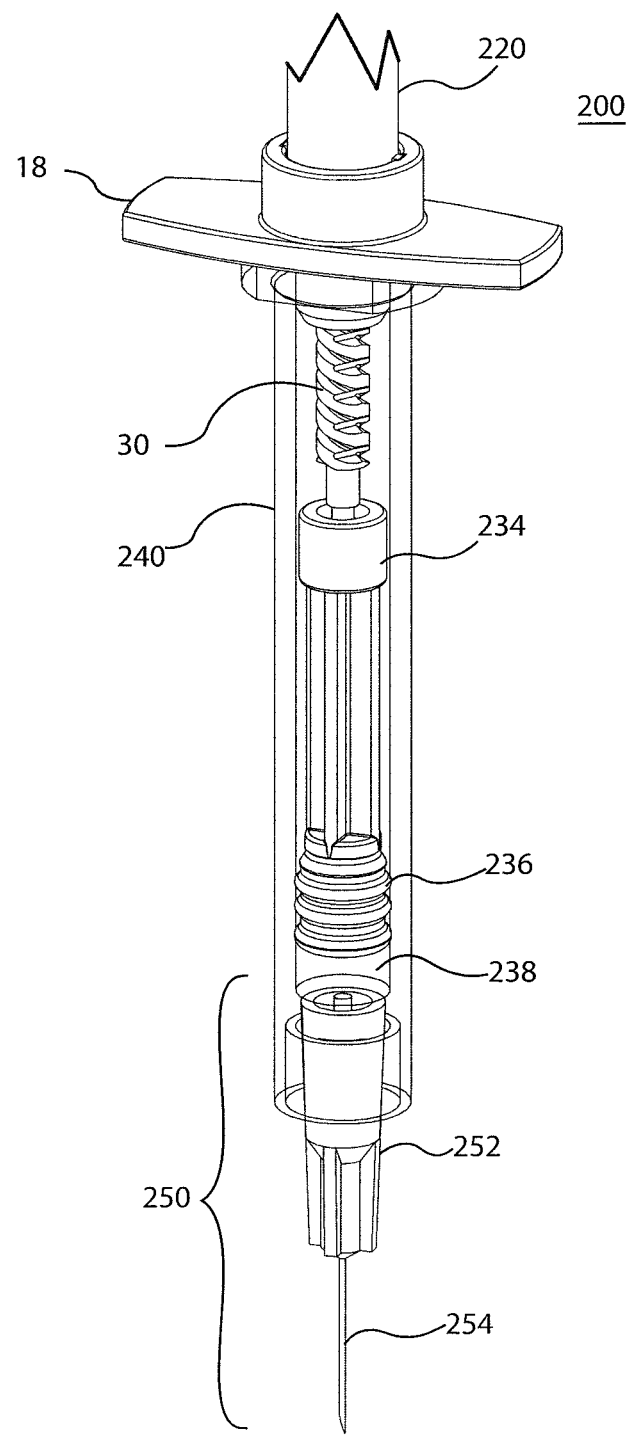
FIG. 5B shows an enlarged isometric view of the distal portion of the drug delivery syringe shown in FIG. 5A.

FIG. 5B shows an enlarged isometric view of the distal portion of the drug delivery syringe shown in FIG. 5A. Screw 30 may be connected to plunger seal 236 either directly or indirectly to drive the axial translation of the plunger seal 236. In the latter configuration, a plunger rod 234 may be utilized between screw 30 and plunger seal 236 to connect those components. The plunger rod 234 may be connected to the screw 30 at, for example, the screw connection 30A aspect. In at least one embodiment, the screw connection aspect is connected to the plunger rod through a proximal opening in the plunger rod such that the screw connection aspect sits within a proximal pocket in the plunger rod. Additionally or alternatively, this connection may be a snap-fit connection, an interference-fit connection, or a number of other connection methods known in the industry. In at least one embodiment, as is described further below with reference to FIGS. 7A-7D, the screw, screw connection aspect, and plunger rod are configured to be readily connectable after the drug chamber has been filled with a drug fluid and the plunger seal and plunger rod have been inserted into the proximal end of the barrel. Preferably, the connection between the screw 30 and the plunger seal 236, or screw 30 and plunger rod 234 when a plunger rod is employed, is such that the screw is permitted to axially rotate while the plunger rod and/or the plunger seal remain rotationally fixed. Accordingly, as the plunger 14 and screw 30 of the control mechanism 10 are axially rotated and translated, the motion is relayed to the plunger seal 236 which is also axially translated. When utilized within a pre-filled syringe, the control mechanism 10 is generally attached to the barrel 240 after the drug chamber 238 of barrel 240 has been filled with a drug fluid. This is often desired so that the syringe 200 may be filled and assembled in standard pharmaceutical fill-finish process lines. Once the syringe 200 has been filled and assembled, the control mechanism 10 may be utilized by the user to identify and set the selected drug dose for delivery. The user may then inject the needle into the patient for drug delivery. Subsequently, the button 16 and/or plunger 14 may be depressed by the user to cause the plunger 14 and screw 30 to axially translate. Because of the function of the control mechanism and the pitch ratio, any measure of distal translation of the plunger 14 causes only an incremental measure of distal translation of the screw 30, permitting accurate dose delivery control by the user. Axial translation of the screw 30 causes axial translation of the plunger seal 236. This axial motion in the distal direction of the plunger seal 236 forces drug fluid out of drug chamber 238 of barrel 240, through the needle 254 of the barrel adapter assembly 250, for injection and delivery to the patient.

Figure 6A:
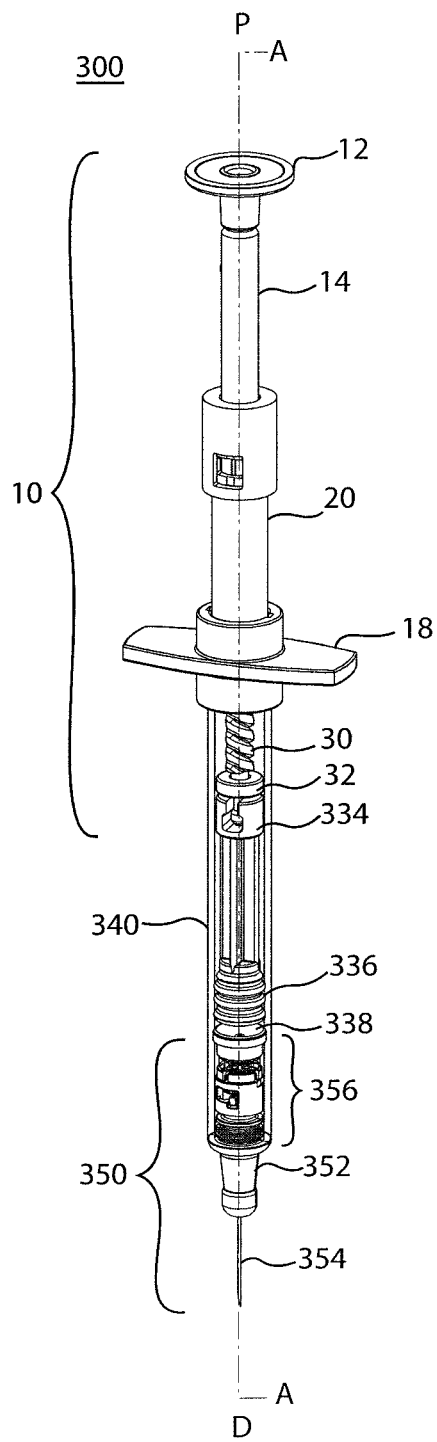
FIG. 6A shows an isometric view of yet another drug delivery syringe which incorporates a dose control mechanism, according to another embodiment of the present invention.

Furthermore, the novel control mechanisms of the present invention may be utilized with safety syringes, such as retractable needle safety syringes (i.e., syringes which incorporate needle safety mechanisms). FIG. 6A shows an embodiment of the dose control mechanism 10 as a component of an exemplary retractable drug delivery syringe 300. As shown, the control mechanism 10 includes a plunger 14, a housing 20, an adapter 18, and a screw 30. The plunger 14 may include a button 12 as a unified or separate component, as described above. Housing 20 may optionally include housing cover 16 at its proximal end, for example, to close the interior of the housing 20 off from the environment, to axially align plunger 14 within housing 20, and/or to prevent accidental removal of plunger 14. Housing 20 may further include a window 20A, which may be an opening (e.g., an aperture) in the housing or a transmissive, translucent, and/or a component providing optical magnification. Plunger 14 may include one or more dose markings 14A on the external surface of the plunger 14. Housing 20 may have one or more reference or guide markings 20B, such as at the window 20A, with which to align or view plunger dose markings 14A. The control mechanism 10 may be attached, mounted, affixed, or otherwise connected at the proximal end of barrel 140 such that at least a portion of the screw 30 resides inside barrel 140.

Figure 6B:
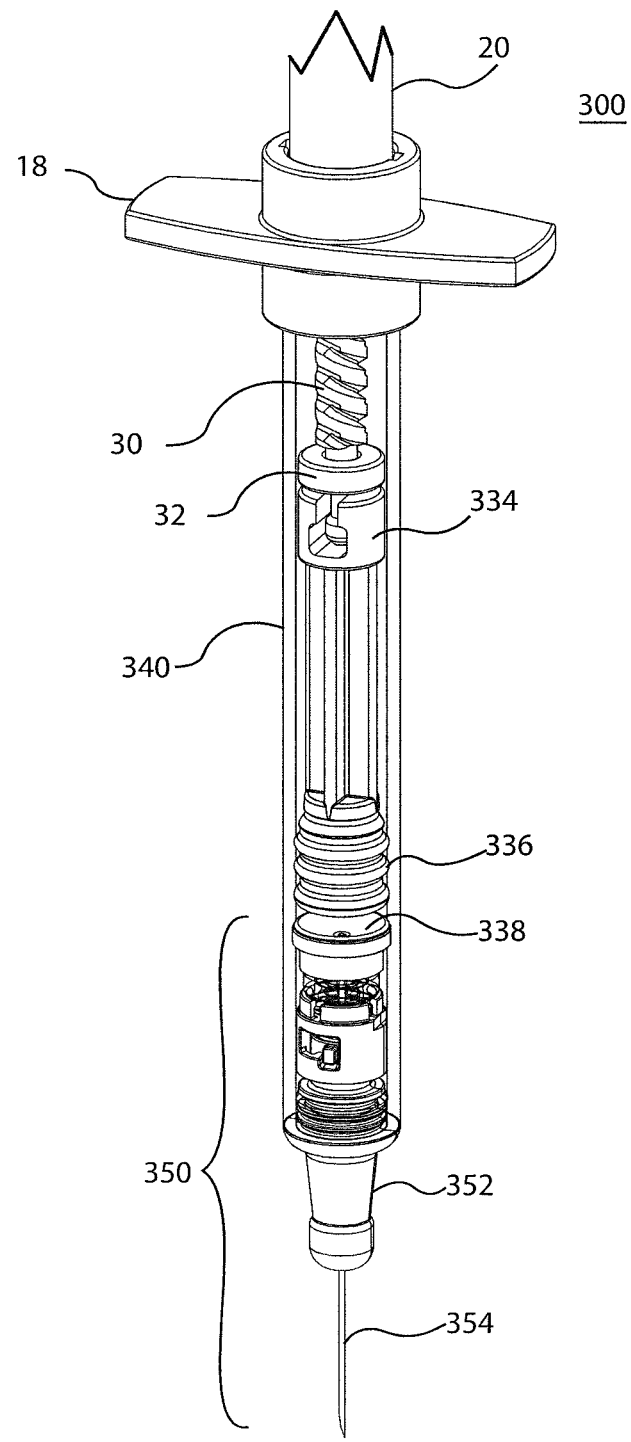
FIG. 6B shows an enlarged isometric view of the distal portion of the drug delivery syringe shown in FIG. 6A.

FIG. 6B shows an enlarged isometric view of the distal portion of the drug delivery syringe shown in FIG. 6A. Screw 30 may be connected to plunger seal 336 either directly or indirectly to drive the axial translation of the plunger seal 336. In the latter configuration, a plunger rod 334 may be utilized between screw 30 and plunger seal 336 to connect those components. The plunger rod 334 may be connected to the screw 30 at, for example, the screw connection 30A aspect. The screw connection aspect may be connected to the plunger rod in the configuration described above with reference to FIGS. 4A and 4B, in the configuration described above with reference to FIGS. 5A and 5B, or any number of other connection methods known in the industry. Preferably, the connection between the screw 30 and the plunger seal 336, or screw 30 and plunger rod 334 when a plunger rod is employed, is such that the screw is permitted to axially rotate while the plunger rod and/or the plunger seal remain rotationally fixed. Accordingly, as the plunger 14 and screw 30 of the control mechanism 10 are axially rotated and translated, the motion is relayed to the plunger seal 336 which is also axially translated. The plunger 14 and screw 30 may function, substantially after the drug dose has been delivered, to initiate or engage a needle retraction or safety mechanism.

When utilized within a safety syringe, such as a retractable needle safety syringe, the plunger 14 of the control mechanism 10 is capable of engaging or initiating a needle safety mechanism. Suitably, the needle safety mechanism is facilitated by a biasing member such as a spring, elastic or other member capable of storing and releasing energy to facilitate needle retraction, needle sheathing, or any other method of protecting the user from accidental needle stick injuries. It will be appreciated that the safety syringe may comprise any needle safety mechanism, such as a needle retraction safety mechanism or needle sheathing safety mechanism, which is operable with the control mechanisms and syringes disclosed herein. By way of example, the needle safety mechanism may be a needle retraction safety mechanism as described in International Publication WO2006/119570, International Publication WO2006/108243, International Publication WO2009/003234, International Publication WO2011/075760, and/or U.S. patent application Ser. No. 13/693,915, although without limitation thereto. In at least one embodiment of the present invention, syringe 300 is a needle retraction safety syringe and incorporates the needle retraction safety mechanism 356 as disclosed in U.S. patent application Ser. No. 13/693,915.

Such a needle retraction safety mechanism 356 may be assembled to the syringe barrel 340, for example as part of the barrel adapter assembly 350, through the distal end of the barrel 340. The control mechanism 10 is generally attached to the barrel 340 after the drug chamber 338 of barrel 340 has been filled with a drug fluid. This is often desired so that the syringe 300 may be filled and assembled in standard pharmaceutical fill-finish process lines. Once the syringe 300 has been filled and assembled, the control mechanism 10 may be utilized by the user to identify and set drug dose for delivery. The user may then inject the needle into the patient for drug delivery. Subsequently, the button 16 and/or plunger 14 may be depressed by the user to cause the plunger 14 and screw 30 to axially translate. Because of the function of the control mechanism and the pitch ratio, any measure of distal translation of the plunger 14 causes only an incremental measure of distal translation of the screw 30, permitting accurate dose delivery control by the user. Axial translation of the screw 30 causes axial translation of the plunger seal 336. This axial motion in the distal direction of the plunger seal 336 forces drug fluid out of drug chamber 338 of barrel 340, through the needle 354 of the barrel adapter assembly 350, for injection and delivery to the patient. At the end of drug delivery, the plunger seal 336 is caused to contact a component of the needle retraction safety mechanism 356 to initiate the retraction mechanism thereby causing retraction of the needle 354 into the barrel 340 of syringe 300. The screw 30 and other components or the control mechanism 10 may be configured or adjusted to permit this additional range of axial translation in the distal direction after the desired drug dose has been delivered. As the needle 354 is then retracted into the barrel 340 of syringe 300, components of the needle retraction safety mechanism 356 bear and push against plunger seal 356 in the proximal direction. As that retraction force is continued, the user may control the rate of needle retraction by controllably reducing the force they apply on the button 12 and/or plunger 14 as the screw 30 and plunger 14 move in the proximal direction. The needle retraction safety mechanism 356 therefore provides a number of additionally desirable features to the novel syringes of the present invention.

As would readily be appreciated by one having ordinary skill in the art, the barrel adapter assembly may be attached, mounted, affixed, or otherwise connected to the distal end of the barrel by a number of known methods. For example, a luer connection may be utilized to connect the barrel adapter assembly to the syringe barrel. Luer connection systems are a standard way of attaching syringes, catheters, hubbed needles, IV tubes, and the like to each other. Luer connections consist of conical/tubular male and female interlocking components slightly tapered to hold together better. Luer connections can either be a "luer slip", as shown in FIGS. 4A and 4B, which are luer connections with a simple pressure or twist fit; or luer connections be a "luer lock", as shown in FIGS. 5A and 5B, which can have an additional outer rim of threading allowing them to be more secure. Alternatively, the connection may be facilitated by a barrel adapter connection. By way of example, the barrel adapter connection may be as described in International Publication WO2011/137488 and/or U.S. patent application Ser. No. 13/693,915, although without limitation thereto. Luer connections, interference fit connections, barrel adapter connections, or any number of other known connections may be utilized to attach the barrel adapter assembly to the barrel while remaining within the breadth and scope of the present invention. Regardless of the type of barrel adapter assembly utilized, the barrel adapter assembly generally comprises of a barrel tip 152, 252, 352 and a needle 154, 254, 354, respectively. In some configurations, the barrel tip 152, 252, 352 may be a pre-formed aspect at the distal end of the barrel. Alternatively, the barrel tip 152, 252, 352 may be a separate component that is attached at the distal end of the barrel. The needle 154, 254, 354 may be any type of fluid conduit including, for example, a flexible cannula or a rigid needle, and may be made of any number of materials, including stainless steel. The type of connections described herein can be utilized regardless of the type of syringe with which they are shown. For clarity, the luer slip connection shown with the fill-at-time-of-use syringe in FIGS. 4A and 4B may be utilized with the pre-filled syringe in FIGS. 5A and 5B, or any other type of connection may be used with any other type of syringe described herein.

It will be appreciated from the foregoing that the novel dose control mechanisms and syringes disclosed herein provide an efficient and easily operated system for the accurate dose setting and delivery of drug treatments. Such devices are safe and easy to use, and are aesthetically and ergonomically appealing for clinical practitioners. The embodiments of the present invention overcome the challenges faced with the use of conventional syringes for the dosing and delivery of low-volume treatments by utilizing novel dose control mechanisms. The novel dose control mechanisms permit the user to accurately read and dose the desired volume of drug treatment for delivery to the patient. These devices permit the user to have a normal range of thumb travel, as they may otherwise expect with a conventional syringe, but transform that range of thumb travel to a very finite (e.g., smaller or incremental) range of plunger seal travel. This relationship allows the user to utilize the syringe without additional training, but with the significant benefit of incremental, low-volume dose control.

Assembly and/or manufacturing of control mechanism 10, syringe 100, syringe 200, or syringe 300, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. For example, a glue or adhesive may be utilized to connect the distal end of the housing 20 to the proximal end of adapter 18. Similarly, a glue or adhesive may be utilized to connect the distal end of adapter 18 to the proximal end of the barrel. Additionally, known siliconization fluids and processes may be employed during the manufacture of the novel components and devices. Furthermore, known sterilization processes may be employed at one or more of the manufacturing or assembly stages to ensure the sterility of the final product.

In one embodiment, a method of assembling the control mechanism includes the steps of:
(i) threading a fine pitch screw at least partially through a fine pitch nut of an adapter;
(ii) threading a plunger, the plunger having a coarse pitch screw on its outer surface and an annular space within its inner surface, at least partially through an interior axial pass-through of housing, wherein the housing interior has a corresponding coarse pitch guide;
(iii) inserting at least a proximal portion of the screw into the annular space of the plunger through a distal portion of the plunger; and
(iv) attaching the outer distal portion of the housing to a proximal aspect of the adapter.

Additionally, the plunger may include a button at its proximal end. The button may be a pre-formed aspect of the plunger or may be a separate component from the plunger. Preferably, the button is a separate component attached to plunger by, for example, snap-fit. Similarly, the housing may include a housing cover at its proximal end. The housing cover may be a pre-formed aspect of the housing or may be a separate component from the housing. As discussed above, a glue or adhesive may be utilized to affix one or more components of the control mechanism to each other. Alternatively, one or more components of the control mechanism may be a unified component. For example, the housing may be a separate component affixed by a glue to adapter, or the adapter may be a preformed aspect at the distal end of the housing which is glued to the barrel. Similarly, the housing cover may be affixed by a glue to the housing. These components may be sterilized individually or together, and may be assembled in a sterile environment or sterilized after assembly. The barrel may be siliconized prior to or after assembly.

The control mechanism may be utilized as a component of a syringe. In one embodiment, the method of manufacturing a syringe comprising a control mechanism includes the steps of:
(i) mounting a barrel adapter assembly to a distal end of a syringe barrel;
(ii) mounting a plunger seal through a proximal end of the syringe barrel; and
(iii) mounting a control mechanism to the proximal end of the syringe barrel, wherein the control mechanism may rest in contact with the plunger seal.

The method of manufacturing a syringe may further comprise, before the step of (ii) mounting a plunger seal through a proximal end of the syringe barrel, the step of: filling the barrel at least partially with a fluid substance. Step (iii) may further require the step of connecting a screw connection aspect of a screw of the control mechanism directly to the plunger or indirectly through a plunger rod which is connected at the proximal end of the plunger seal. The connection between the plunger rod and the plunger seal may be any number of connections including, but not limited to, screw-type connection, snap-fit connections, interference connections, capture connections, and the like. In at least one embodiment, the screw connection aspect is connected to the plunger rod through a radial opening or a proximal opening in the plunger rod such that the screw connection aspect sits within a proximal pocket in the plunger rod. Additionally or alternatively, this connection may be a snap-fit connection, an interference-fit connection, or a number of other connection methods known in the industry. Preferably, the connection between the screw and the plunger seal, or between the screw and plunger rod when a plunger rod is employed, is such that the screw is permitted to axially rotate while the plunger rod and/or the plunger seal remain rotationally fixed.

Figure 7A:
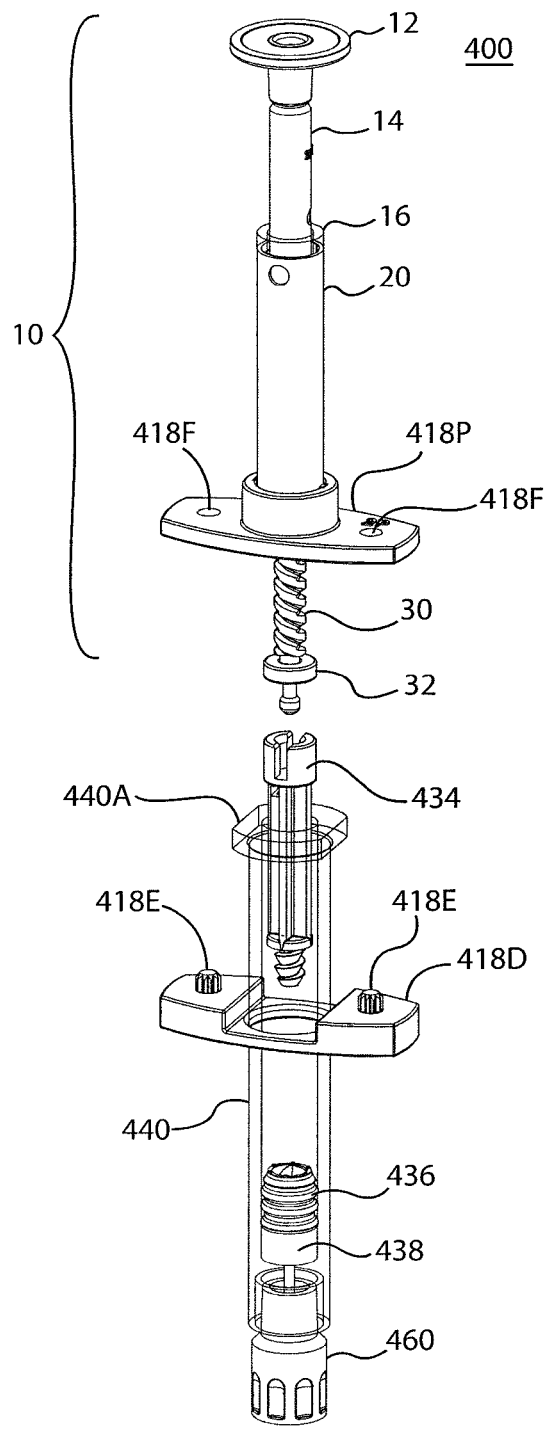
FIG. 7A shows an isometric view of an initial assembly stage of a pre-filled drug delivery syringe which incorporates a dose control mechanism, according to at least one embodiment of the present invention.

One preferred method of manufacturing a syringe having a dose control mechanism, according to one embodiment of the present invention, is described herein with reference to FIGS. 7A-7D. FIG. 7A shows a pre-filled syringe, such as that described with reference to FIGS. 5A-5B above, wherein the adapter is a two-component adapter having a proximal adapter portion 418P and a distal adapter portion 418D. Proximal adapter portion 418P has one or more connection prongs 418E and distal adapter portion 418D has corresponding connection ports 418F. When forced together, connection prongs 418E and corresponding connection ports 418F merge, mate, or otherwise connect to unite the two portions of the adapter 418P, 418D. Initially, a cap 460 may be connected to the distal end of barrel 440 of syringe 400. The distal adapter portion 418D may be slidably mounted to the exterior of the barrel. The interior of the barrel 440, i.e. the drug chamber 438, may be filled with a drug fluid or substance through the open proximal end of the barrel. The plunger seal 436 may be mounted into the barrel through the proximal end such that is in contact with the fluid. The optional plunger rod 434 may be connected to the plunger seal 436 prior to, or after, insertion of the plunger seal 436 into the barrel 440. These steps may be performed in a sterile environment to maintain the container integrity and sterility of the drug treatment.

Figure 7B:
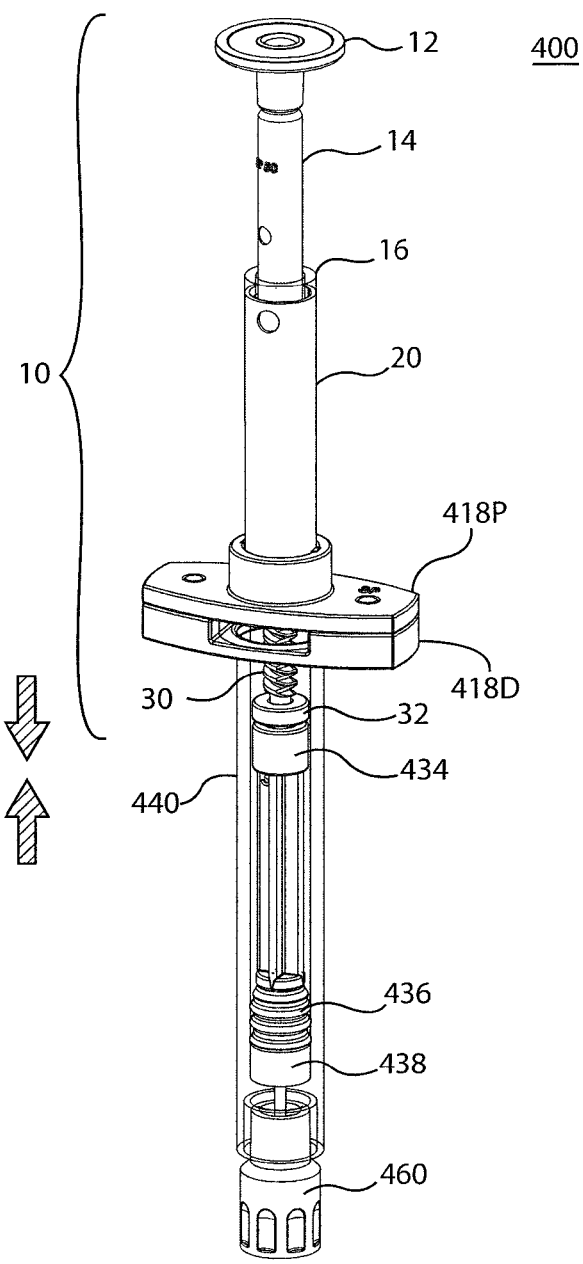
FIG. 7B shows an isometric view of the pre-filled drug delivery syringe shown in FIG. 7A after it has been assembled.
Figures 7C, 7D:
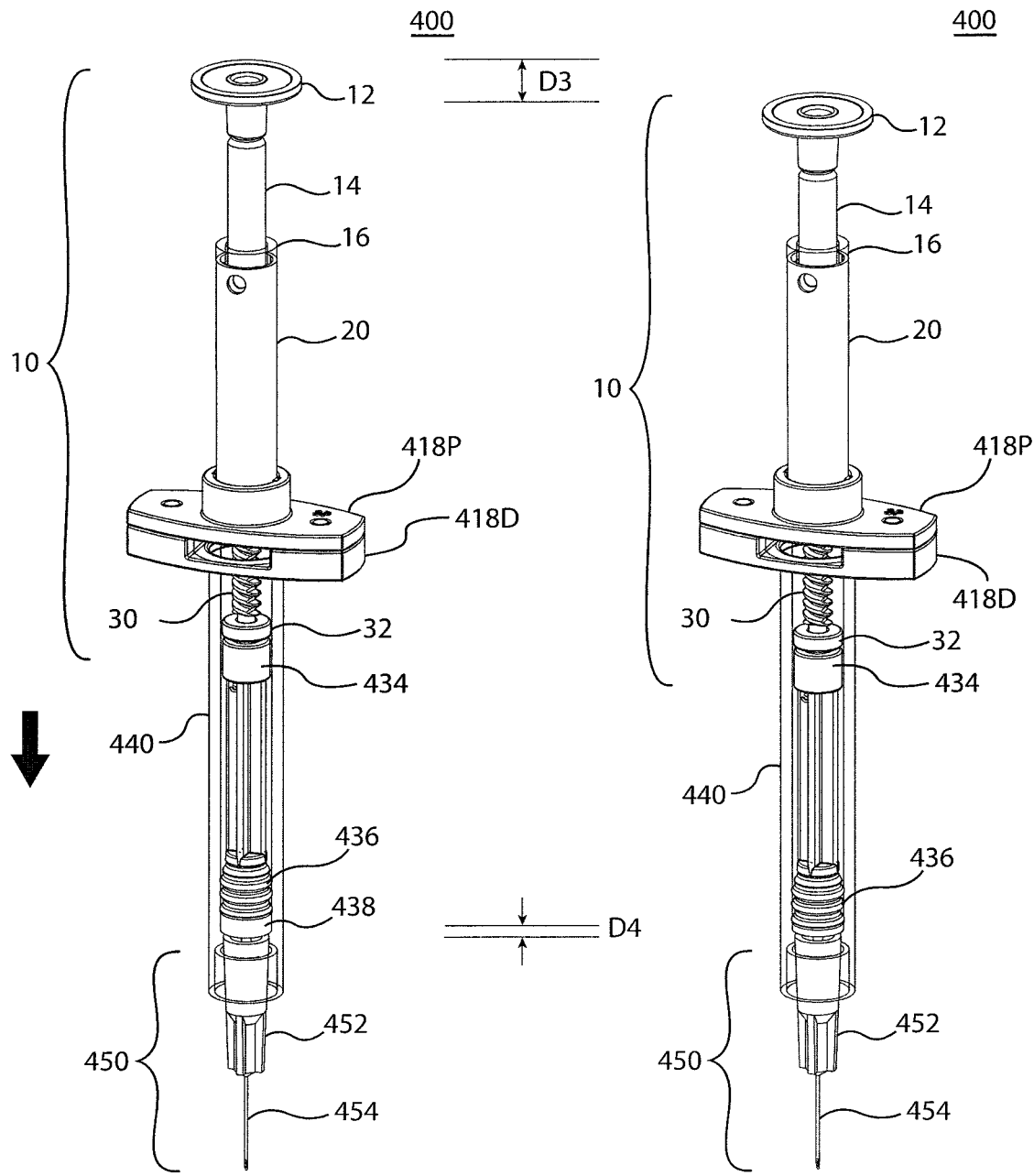
FIG. 7C shows an isometric view of the pre-filled drug delivery syringe shown in FIG. 7A in a ready-to-inject stage of operation.
FIG. 7D shows an isometric view of the pre-filled drug delivery syringe shown in FIG. 7A in an end-of-dose stage of operation.

The remainder of the syringe may then be assembled in a non-sterile or sterile environment. The screw, as a component of the control mechanism, may then be connected to the plunger seal or to the plunger rod when a plunger rod is employed. The distal adapter portion 418D may then be slid in the proximal direction along the exterior of the barrel to connect to the proximal adapter portion 418P as described above. The connection between the distal adapter portion 418D and the proximal adapter portion 418P may capture a barrel flange 440A aspect of the barrel 440 in order to retain the control mechanism 10 at the proximal end of the barrel 440. Various glues or adhesives may be utilized to ensure that such components and connections are retained in position during assembly, filling, manufacturing, transportation, storage, and operation of the novel devices of the present invention. The final assembly of the syringe, such as in the pre-filled syringe 400, may appear as shown in FIG. 7B. This type of pre-filled syringe may be utilized when, for example, a syringe is to be filled with a standard amount of drug fluid by a pharmaceutical company or contract drug filler, when the drug dose is variably selectable by the user, when the needle length is variably selectable by the user, or in a number of other situations. FIG. 7C shows the pre-filled syringe with a selectable needle that is attached via a luer lock connection, as described above. In such a scenario, the syringe may be held such that the distal end of the syringe is pointed upwards. The cap 460 (shown in FIG. 7B) may be removed and replaced by a barrel adapter assembly 450. The barrel adapter assembly 450 includes a barrel tip 453 and needle 454 which may be selected by the user and attached to the pre-filled syringe just prior to use. The drug dose may be identified and selected by the user, as described above. Comparison of the pre-filled syringe 400 in FIGS. 7C and 7D clarifies the differences in the pre-filled syringe just prior to, and after, injection and delivery of the drug dose to the patient. Because of the pitch ratio between the plunger 14 and the screw 30, screw 30 is caused to axially translated in the distal direction only incrementally or to a lesser distance when plunger 14 is depressed or axially translated in the distal direction (i.e., in the direction of solid arrow in FIGS. 7C and 7D). This difference in axial translation distance between plunger 14 and screw 30 is visible by comparing distances D3 and D4 in FIGS. 7C and 7D. D3 is the distance that plunger 14 axially translates while D4 is the fractional distance that screw 30 axially translates.

Accordingly, the novel embodiments of the present invention provide dose control mechanisms, which allow for the accurate dosing and delivery of drug treatments, and drug delivery syringes which incorporate such control mechanisms. Such novel devices permit the identification and control of the dosage amount, permit the syringe to be "primed" (i.e., evacuated of air bubbles) prior to drug delivery, and ensure the accurate delivery of microliter volume dosages, all within a device size that is similar to commonly used conventional syringes available in the marketplace. Such novel devices are safe and easy to use, and are aesthetically and ergonomically appealing for clinical practitioners. The novel devices of the present invention provide these desirable features without any of the problems associated with known prior art devices.

A number of known filling processes and equipment may be utilized to achieve the filling steps of the syringe manufacturing process. The barrel assembly, needle, plunger seal, plunger rod, and other components described in these manufacturing and assembly processes may be as described above or may be a number of similar components which achieve the same functionality as these components. Throughout the specification, the aim has been to describe the preferred embodiments of the invention without limiting the invention to any one embodiment or specific collection of features. Various changes and modifications may be made to the embodiments described and illustrated without departing from the present invention. The disclosure of each patent and scientific document, computer program and algorithm referred to in this specification is incorporated by reference in its entirety.

What is claimed is:

1. A dose control mechanism for a syringe comprising:
a housing having an interior surface including a course pitch guide;
a plunger having an exterior surface and an internal annular space, the internal annular surface including a first key aspect, the exterior surface including a coarse pitch screw, the plunger residing at least partially within the housing, the coarse pitch guide along the interior surface of the housing interfacing with the course pitch screw of the plunger; and
a screw having a second key aspect and a fine pitch screw which interfaces with a fine pitch nut of an adapter;
wherein the screw at least partially resides in the internal annular space of the plunger, the first key aspect of the plunger and the second key aspect of the screw being directly engaged such that rotational movement of the plunger directly causes rotational movement of the screw.

2. The dose control mechanism of claim 1, wherein a pitch ratio between the coarse pitch screw and the fine pitch screw is from approximately 1:1 to approximately 20:1.

3. The dose control mechanism of claim 1, wherein a pitch ratio of the coarse pitch screw and the fine pitch screw is selected from the group consisting of approximately 4:1, approximately 3:1, and approximately 2:1.

4. The dose control mechanism of claim 1, wherein the screw has a screw connection aspect and, optionally, a ring.

5. The dose control mechanism of claim 1, wherein the housing has a proximal end and a housing cover at the proximal end of the housing, the housing further including a window to permit the user to view the location of the plunger within the housing.

6. The dose control mechanism of claim 1, wherein the plunger has one or more dose markings on the exterior surface of the plunger and the housing has one or more guide markings with which to align the plunger dose markings to set a dose.

7. The dose control mechanism of claim 1, wherein, upon depression of the plunger into the housing, the plunger axially translates a first distance (D1) causing the screw to axially translate a second distance (D2), and wherein the first distance (D1) is greater than the second distance (D2).

8. An accurate dose drug delivery syringe comprises a dose control mechanism, a barrel, a plunger seal, and a barrel adapter assembly having a barrel tip and a needle, wherein the dose control mechanism comprises a plunger having an internal annular space with a first key aspect and a coarse pitch screw on an exterior surface of the plunger; a housing having a coarse pitch guide along an interior surface of the housing which interfaces with the course pitch screw of the plunger; and a screw having a second key aspect and a fine pitch screw which interfaces with a fine pitch nut of an adapter; wherein the screw at least partially resides in the internal annular space of the plunger and the first key aspect of the plunger and second key aspect of the screw are directly engaged such that rotational movement of the plunger directly causes rotational movement of the screw.

9. The syringe of claim 8, wherein the plunger having the coarse pitch is rotatable upon the corresponding coarse pitch guide, and wherein at least a portion of the plunger interfaces with some portion of screw, such that the two are rotationally keyed.

10. The syringe of claim 8, wherein a pitch ratio between the coarse pitch screw and the fine pitch screw is from approximately 1:1 to approximately 20:1.

11. The syringe of claim 8, further comprising a plunger rod connected at one end to the screw and at another end to the plunger seal.

12. The syringe of claim 8, wherein the syringe is a fill-at-time-of-use syringe, a pre-filled syringe, or a safety syringe, or a combination thereof.

13. The syringe of claim 8, wherein the housing has a housing cover at a proximal end of the housing and a window to permit the user to view the location of the plunger within the housing, the plunger has one or more dose markings on the exterior surface of the plunger, and the housing has one or more guide markings at the window with which to align plunger dose markings.

14. The syringe of claim 8, wherein, upon depression of the plunger into the housing, the plunger axially translates a first distance (D3) causing the screw to axially translate a second distance (D4).

* * * * *